(12) United States Patent
Creeth et al.

(10) Patent No.: US 6,290,975 B1
(45) Date of Patent: Sep. 18, 2001

(54) METHOD FOR THE PREVENTION OF GUM DISEASE

(75) Inventors: Jonathan Edward Creeth; William John Stead, both of Bebington; David Michael Williams, London, all of (GB)

(73) Assignee: Unilever Home & Personal Care USA, division of Conopco, Inc., Greenwich, CT (US)

(*) Notice: Subject to any disclaimer, the term of this patent is extended or adjusted under 35 U.S.C. 154(b) by 0 days.

(21) Appl. No.: 09/312,275

(22) Filed: May 14, 1999

(30) Foreign Application Priority Data

May 15, 1998 (GB) .................................................. 9810521
Nov. 12, 1998 (GB) .................................................. 9824875

(51) Int. Cl.[7] ................................. A61K 6/00; A61K 7/00
(52) U.S. Cl. ............................................................. 424/401
(58) Field of Search ................................... 424/400, 401, 424/49

(56) References Cited

U.S. PATENT DOCUMENTS

| 4,409,202 | 10/1983 | Witzel et al. . |
| 4,971,788 | 11/1990 | Tabibi et al. . |
| 5,100,919 | 3/1992 | Ulrich et al. . |
| 5,344,641 | 9/1994 | Gaffar et al. . |
| 5,637,290 | 6/1997 | Sodis et al. . |
| 5,833,955 | 11/1998 | Kleinberg et al. . |

FOREIGN PATENT DOCUMENTS

| 34 07 860 | 3/1984 | (DE) . |
| 0 450 598 | 3/1991 | (EP) . |
| 0 470 019 | 5/1992 | (EP) . |
| 709132 | 5/1954 | (GB) . |
| 796498 | 6/1958 | (GB) . |
| 2 219 937 | 12/1989 | (GB) . |
| 58128313 | 7/1983 | (JP) . |
| 2078576 | 5/1997 | (RU) . |
| 92/02216 | 2/1992 | (WO) . |
| 93/01723 | 2/1993 | (WO) . |
| 95/35351 | 12/1995 | (WO) . |
| 96/26707 | 9/1996 | (WO) . |
| 97/15277 | 5/1997 | (WO) . |

*Primary Examiner*—Dameron L. Jones
(74) *Attorney, Agent, or Firm*—Milton L. Honig

(57) ABSTRACT

A method is provided which treats or prevents gum disease involving applying to the gums an agent for maintaining or improving the permeability barrier of the gum.

3 Claims, 1 Drawing Sheet

METHOD FOR THE PREVENTION OF GUM DISEASE

BACKGROUND OF THE INVENTION

1. Field of the Invention

Figure 1:
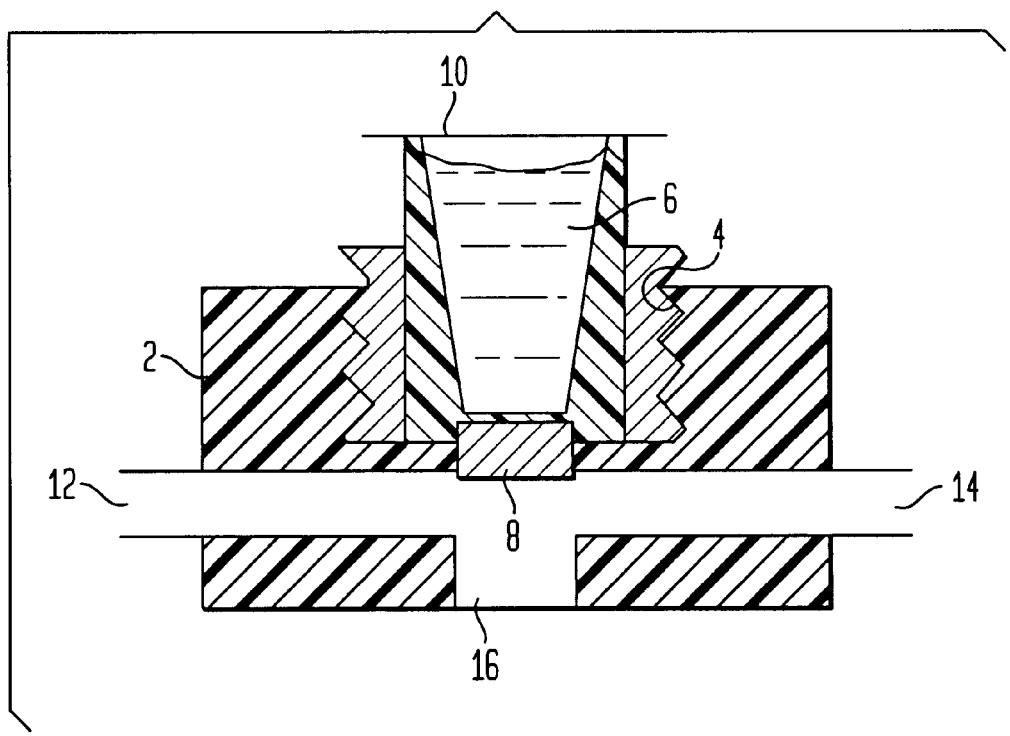

The present invention relates to the use of an agent which maintains or improves the permeability barrier of the gum in the manufacture of an oral composition for the treatment or prevention of gum disease.

2. The Related Art

Efficient dental hygiene is a primary requirement in maintaining good oral health. Poor oral health manifests itself in many forms, for example tooth decay, gum disease, mouth ulcers etc.

In addition, stained teeth and diseased gums are a cosmetically undesirable consequence of poor oral hygiene.

Improved oral hygiene is, therefore, a much sought goal and there is much prior art relating to various methods which may be employed in achieving this consumer positive. For example, antimicrobial agents such as chlorhexidine and Triclosan (2', 4,4'-trichloro, 2-hydroxy-diphenyl ether) have been used in dentifrice compositions and are employed to reduce bacterial build up and, therefore, plaque production on the teeth. Reducing the formation of plaque helps reduce the staining of teeth and also helps prevent gum disease.

Despite these prior proposals, there is still a need for an effective method for improving oral care.

We have now surprisingly found, that providing a protective barrier over the gum is capable of providing an improved benefit in oral hygiene.

It is thought that by improving the permeability barrier of the gum that the cosmetic disadvantages of gum disease can be prevented.

SUMMARY AND DETAILED DESCRIPTION OF THE INVENTION

Accordingly the invention concerns the use of an agent which maintains or improves the permeability barrier of the gum in the manufacture of an oral composition for the treatment or prevention of gum disease.

Preferably, the agent is capable of reducing the permeability coefficient of the gum by at least 20%, more preferably at least 30% and especially by at least 40% with respect to the coefficient effected by phosphate buffered saline (PBS).

More preferably the agent is a fat or an oil, most preferably an oil and especially an oil selected from the group consisting of silicone oil, vegetable oil, animal oil and mineral oil.

An alternative agent according to the invention is a synthetic ester such as isopropyl myristate.

Where the agent is a fat it is preferable that it is a fat, e.g. a triglyceride, with a melting point of below 50° C.

By oral composition is meant any composition applied to the oral cavity, e.g. toothpaste, mouthwash, gel, cream, powder, lozenge, mousse, etc. It may also be a composition formulated in a multi-compartment type dispenser. Typically, the agent will comprise almost entirely of the agent; preferably from 0.01 to 30%, more preferably from 0.1 to 20% and especially from 0.1 to 10% by weight of the oral position according to the invention.

The present invention will be further illustrated by way of example.

EXAMPLE

| Sample | |
| --- | --- |
| 1 | PBS (1) |
| 2 | Akogel (2) |
| 3 | Sunflower oil (3) |
| 4 | Borage oil (4) |
| 5 | Petroleum jelly (5) |
| 6 | silicane oil (6) |
| 7 | silicane oil (7) |

(1) Phosphate buffered saline
(2) Vegetable fat ex Karlshamns (Lot 4594 1996-02-22)
(3) ex Anglia oils (753-97 RBWD)
(4) ex Anglia oils
(5) White soft paraffin jelly ex Hansen & Rosenthal Pioneer (6954)
(6) Heavy silicane ex Dow Corning (DC200/5000 cps)
(7) Light silicane ex Dow Corning (DC200/350 cps)

Specimens of gingiva were obtained from animals used for surgical research. The gingiva was taken from the region between the incisor and premolar teeth in the maxilla. The specimens were taken within 2 hours of death, excess muscle and fat removed and the tissue was snap frozen in liquid nitrogen and stored at −70° C. until use.

The specimen was thawed completely before use in the permeability experiment. In order to prevent cracking during thawing, the specimen was placed in a plastic petri-dish at room temperature for 5–10 min. The specimen was then removed from PBS and the epithelium was damped dry. Pieces of tissue, about 6 mm in diameter, were cut from the specimen using a blade, excess muscle was removed. Lipids were extracted from excised gum tissue using chloroform-:methanol (2:1 v/v) containing 1% hydrochloric acid and 4% water. The tissue was immersed for 60 min in this mixture and then washed with PBS prior to treatment with the agent. The agent had been applied to each piece, which was clamped between the two parts of the chamber described below.

Application of agents

The following protocol was used to deliver the agent:

The tissue was rinsed in PBS and blotted dry. The agent was applied by brushing gently and evenly over the epithelial surface of the tissue using an interspace toothbrush. The treated tissue was left for 1 min and then rinsed in PBS by dipping 5 times in 5 s.

The treated tissue was then loaded into flow through chambers for the permeability experiment.

BRIEF DESCRIPTION OF THE DRAWINGS AND PERMEABILITY EXPERIMENT

The permeability of the treated tissue to the tritiated water was measured using the Teflon flow through chamber provided by the Crown Glass Company, USA as presented in FIG. 1. This apparatus includes a teflon chamber 2 provided with an aperture defined by a threaded collar 4 for receiving therein a reservoir 6 of tritiated water. A tissue receiving member 8 is inserted below the reservoir 6. Test agents may be placed on the tissue receiving member. A cover slip 10 prevents evaporation of water from the reservoir. The teflon chamber is fitted with an inlet port 12 and an outlet port 14 as well as a viewing port 16, the latter allowing visualization of any air bubbles.

Pieces of treated tissue 6 mm in diameter were clamped into the tissue receiving member, exposing an area of epithelium 3 mm in diameter to the reservoir.

The chambers were placed onto a rack which has water circulating through at 37° C. in order to maintain the tissue at physiological temperature and PBS was passed across the connective tissue side at 3–4 ml h$^{-1}$. A 450 µl aliquot of 5 mCi ml$^{-1}$ tritiated water was added to the epithelial compartment and samples from the connective tissue side were collected hourly up to 8 hours. The amount of isotope passing across the epithelium was measured using a Beckman LS6000SC scintillation counter.

The permeability coefficient (Kp) was calculated using the formula:

$$Kp = Q/A*t(C_0-C_1)$$

where Q is the concentration of the tritiated water crossing the treated tissue in time interval t (mins), $C_0$–$C_1$ are the concentrations of the tritiated water on the epithelial and connective tissue sides of the treated tissue respectively, and A is the area of treated tissue exposed to the tritiated water (cm$^2$). The units of Kp are cm min$^{-1}$.

The permeability coefficient is the measure of permeability of the treated tissue to tritiated water.

Table 1 shows the permeability coefficients effected by the sample agents listed above.

TABLE 1

| Sample | Permeability coefficient (x10$^{-4}$ cm min$^{-1}$) |
|---|---|
| 1 | 18.08 |
| 2 | 11.68 |
| 3 | 11.80 |
| 4 | 12.83 |

TABLE 1-continued

| Sample | Permeability coefficient (x10$^{-4}$ cm min$^{-1}$) |
|---|---|
| 5 | 15.20 |
| 6 | 12.61 |
| 7 | 11.88 |

Compared with the control sample (PBS) it can clearly be seen that all of the sample agents decrease the permeability of the gum epithelium to some degree. However, it can be seen that some are better than others. Akogel and light silicone oil were particularly useful at improving the permeability barrier of the gum whereas petroleum jelly was less useful.

What is claimed is:

1. A method for treatment of gum disease comprising applying to gums having a permeability barrier defined by a permeability coefficient, an agent which is sunflower oil for improving the permeability barrier by reducing the permeability coefficient of the gum by at least 20%.

2. The method according to claim 1 wherein the agent reduces the permeability coefficient of the gum by at least 30%.

3. The method according to claim 1 wherein the agent reduces the permeability coefficient of the gum by at least 40%.

* * * * *